United States Patent [19]

Schachar

[11] 4,300,818
[45] Nov. 17, 1981

[54] MULTIFOCAL OPHTHALMIC LENS

[76] Inventor: Ronald A. Schachar, 213 N. Barrett, Denison, Tex. 75020

[21] Appl. No.: 885,942

[22] Filed: Mar. 13, 1978

[51] Int. Cl.³ .................. A61B 3/14; G02C 1/00; G02C 7/02; G02F 1/13
[52] U.S. Cl. .................... 351/7; 351/41; 351/158; 351/159; 350/331 R
[58] Field of Search .......... 351/41, 159, 168, 7, 351/158; 350/331

[56] References Cited
U.S. PATENT DOCUMENTS

| | | | |
|---|---|---|---|
| 3,309,162 | 3/1967 | Kosanke et al. | 350/160 |
| 3,379,885 | 4/1968 | Nork | 351/158 UX |
| 3,424,513 | 1/1969 | Lotspeich | 350/180 |
| 3,473,868 | 9/1972 | Young et al. | 351/39 |
| 3,525,565 | 8/1970 | O'Neill et al. | 351/6 |
| 3,533,683 | 11/1971 | Stark et al. | 351/32 |
| 3,533,684 | 10/1970 | Stark et al. | 351/1 |
| 3,551,026 | 12/1970 | Heilmeier | 350/150 |
| 3,583,794 | 4/1971 | Newman et al. | 351/6 |
| 3,598,479 | 8/1971 | Wright | 351/159 |
| 3,614,215 | 10/1971 | Mackta | 351/41 |
| 3,623,799 | 11/1971 | Millodot | 351/32 |
| 3,641,354 | 2/1972 | De Ment | 250/216 |
| 3,679,295 | 7/1972 | Newman et al. | 351/6 |
| 3,689,135 | 9/1972 | Young et al. | 351/39 |
| 3,803,408 | 4/1974 | Assouline et al. | 250/213 R |
| 3,857,629 | 12/1974 | Freiser | 350/160 LC |
| 3,877,798 | 4/1974 | Tolar et al. | 351/168 |
| 3,930,715 | 1/1976 | Brumlik | 350/160 R |
| 3,951,527 | 4/1976 | Blanz | 351/30 |
| 3,961,181 | 6/1976 | Golden | 250/208 |
| 3,984,156 | 9/1974 | Jernigan | 351/6 |
| 4,037,929 | 7/1977 | Bricot | 350/160 LC |
| 4,039,254 | 5/1976 | Harsch | 350/160 LC |
| 4,059,348 | 11/1977 | Jernigan | 351/30 |
| 4,078,856 | 3/1978 | Thompson et al. | 350/362 |
| 4,181,408 | 1/1980 | Senders | 351/7 |
| 4,190,330 | 2/1980 | Berreman | 350/331 |

Primary Examiner—John K. Corbin
Assistant Examiner—Rodney B. Bovernick
Attorney, Agent, or Firm—Richards, Harris & Medlock

[57] ABSTRACT

The specification discloses a multifocal ophthalmic lens to provide a variable focusing power lens for near and farsighted corrected vision. The lens includes a first and second lens element. First and second electrodes are disposed between the lens elements, and a film of liquid crystal is disposed between the electrodes. A voltage supply source is provided for applying a voltage to the electrodes to vary the index presented by the liquid crystal film to thereby provide a variation in the index of refraction and focal length of the lens elements. Circuitry is provided for varying the voltage applied to the electrodes to determine the focusing power of the lens.

3 Claims, 8 Drawing Figures

MULTIFOCAL OPHTHALMIC LENS

FIELD OF THE INVENTION

This invention relates to ophthalmic lenses, and more particularly relates to multifocal ophthalmic lenses utilizing a liquid crystal to vary the focusing power of the lens.

THE PRIOR ART

With increasing age, the power of accommodation of the human eye decreases. Accommodation is the ability to vary the focal length of the eye lens when viewing near or distant objects. The focal length of the eye is varied by adding refractive power to the eye by increasing the curvature of the crystalline lens. The total increase in the power that the lens can produce is known as the amplitude of accommodation. The amplitude of accommodation is greatest in children, when the crystalline lens is softest. A child, by virtue of a large amplitude of accommodation, is able to hold print close to his eyes and read without the use of supplementary lenses. However, with increased age, as the crystalline lens becomes more rigid, a condition known as presbyopia may develop.

Heretofore, a common method of compensating for the lack of accommodation has been to use bifocal or even trifocal lenses. Bifocal and trifocal lenses are composite lenses built up from lenses of differing but fixed focal lengths. Such lenses bring objects at specific near and far distances into sharp focus. However, since these lenses are for discrete distances, some additional accommodation on the part of the user of such lenses is still required. For example, for distances lying between the two focal lengths of a bifocal lens, the user must accommodate for these distances as only objects falling within the focal length of the bifical lens are brought into sharp focus.

Although bifocal lens eliminate the inconvenience of two pairs of glasses, the psychology of wearing bifocals presents significant problems to the user. Many individuals have difficulty in adapting to the use of bifocals and experience difficulties from the nature of their occupations in viewing objects at different distances through specific areas of the lenses. Furthermore, the user of bifocal lenses is generally forced to utilize a specific portion of the lens when not actually necessary. For example, when walking down steps it is normal for a person to look down at the steps. The viewing of the steps requires the bifocal user to view the steps through the lower portion of the lens that beings the steps into closer focus as for reading, but which is not necessary for this type of viewing where the user should be viewing the steps through the upper portion of the bifocal lens.

Where bifocals are not adequate for intermediate distances, trifocal lenses have been utilized; however, this type of lens presents similar problems associated with bifocal lenses. With both bifocal and trifocal lenses, the prescriptions therefor must be periodically changed, thus requiring the purchase of a new set of glasses.

Another condition associated with problems in accommodation is accommodation esotropia present in farsighted children. Bifocal lenses offer some compensation for this defect; however, children have a tendency to avoid using the bifocal portion of the lens by viewing objects over the bifocal lens.

A need has thus arisen for a multifocal ophthalmic lens to compensate for decreasing powers of accommodation of the human eye with age. Additionally, a need has arisen for a multifocal ophthalmic lens which does not include discrete focal lengths, but includes varying focal lengths to provide accommodation for both near and far distances while allowing the user to view both near and far distances through the center of the lens or any part of the lens.

SUMMARY OF THE INVENTION

In accordance with the present invention, a multifocal ophthalmic lens includes a liquid crystal film for varying the power of a lens to thereby provide accommodation for the user throughout a range of viewing distances.

In accordance with another aspect of the present invention, a multifocal ophthalmic lens to provide for corrected vison of a user includes first and second lens elements. Disposed adjacent the first and second lens elements are first and second electrodes. A film of liquid crystal is disposed between the two electrodes. A voltage supply source for applying a voltage to the electrodes is provided to vary the index presented by the liquid crystal film to thereby vary the focal length of the lens elements. Circuitry is provided to vary the voltage applied to the electrodes to determine the focusing power of the lens.

In accordance with another aspect of the present invention, a multifocal ophthalmic lens adapted to be selectively controlled to vary the focal length of the lens is provided for near and farsighted corrected vision and includes first and second lens elements. The first and second lens elements have inner and outer wall surfaces such that the outer surface of the first lens element lies adjacent the inner surface of the second lens element. A first electrode is disposed adjacent the outer surface of the first lens element. A second electrode is disposed adjacent the inner surface of the second lens element. A film of liquid crystal is disposed between the two electrodes. A voltage supply source is provided for generating a variable voltage for application to the electrodes to vary the index presented by the liquid crystal film. In response to application of the variable voltage to the electrodes, the liquid crystal film causes the focal length of the lens elements to change. First and second light sources are mounted adjacent the lens elements for generating first and second beams of light directed to impinge upon the eyes of the user. Light detecting elements are mounted adjacent the lens elements for detecting reflections of the beams of light reflected from the eyes of the user. The first and second light sources and the detecting elements track the convergent movement of the eyes of the user for near and distant vision. Circuitry is provided to generate a control signal in response to the detecting elements for application to the voltage supply source, such that the reflection intensity of said beams of light varies the control signal to thereby control the focusing power of the lens.

DESCRIPTION OF THE DRAWINGS

For a more complete understanding of the present invention and for other objects and advantages thereof, reference is now made to the following description, taken in conjunction with the accompanying drawings, in which.

DESCRIPTION OF THE PREFERRED EMBODIMENT

Figure 1:
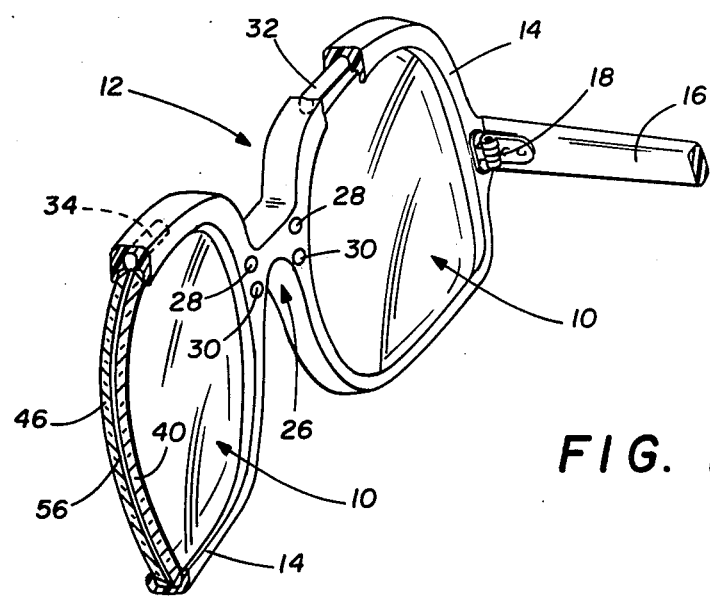
FIG. 1 is a perspective view of an eyeglass frame in which the present multifocal ophthalmic lens is mounted.

Referring to FIG. 1, the multifocal ophthalmic lens of the present invention is generally identified by the numeral 10. Multifocal ophthalmic lens 10 is mounted into an eyeglass frame generally identified by the numeral 12. Eyeglass frame 12 includes a lens mounting number 14 and a temple member 16 secured to each other by a conventional hinge member 18.

FIG. 1 also illustrates the eye tracking system of the present invention generally identified by the numeral 26. Tracking system 26 functions to monitor the convergent position of the eyes of the user of the multifocal ophthalmic lens 10. Tracking system 26 includes low intensity light sources 28 which may comprise, for example, light emitting diodes. Mounted adjacent light sources 28 are light detectors 30 which may comprise for example, photodiodes for detecting a reflection of the light beams generated by light sources 28 and reflected from the eyes of the user. The operation of the tracking system 26 will be subsequently described in connection with FIGS. 3–7.

Mounted within lens mounting member 14 of eyeglass frame 12 are voltage supply sources 32 and 34 and related circuitry. Voltage supply sources 32 and 34 in the preferred embodiment comprise 1.35 volt batteries to supply power to the tracking system 26 and multifocal ophthalmic lens 10.

Figure 2:
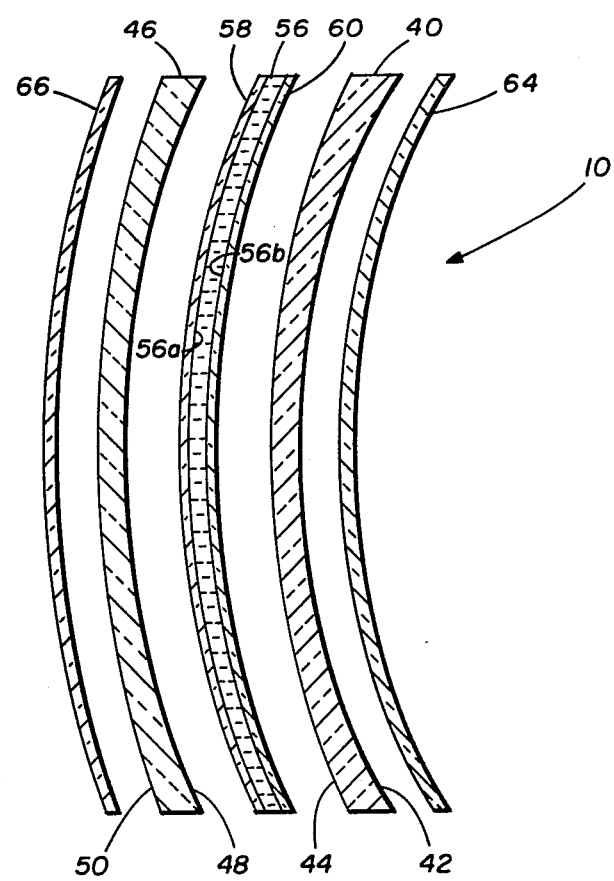
FIG. 2 is a cross-sectional exploded view of the multifocal ophthalmic lens of the present invention.

Referring simultaneously to FIGS. 1 and 2, the construction of multifocal ophthalmic lens 10 will now be discussed. Multifocal ophthalmic lens 10 includes a lens element 40 having an inner concave surface 42 and an outer convex surface 44. A second lens element 46 is included within multifocal ophthalmic lens 10 and includes an inner concave surface 48 and an outer convex surface 50. A layer or film of liquid crystal 56 is disposed between outer convex surface 44 of lens element 40 and inner concave surface 48 of lens element 46. Liquid crystal film 56 may comprise for example cyanodiphenyl material.

Mounted to outer surface 56a and inner surface 56b of liquid crystal film 56 are transparent electrodes 58 and 60. Electrodes 58 and 60 may comprise a mixture of tin oxide and indium oxide applied to liquid crystal film 56 using conventional techniques well known in the art.

An important aspect of the present invention is that by application of a variable voltage potential to electrodes 58 and 60, the index of refraction of the liquid crystal film 56 can be selectively changed. The variation in the index of refraction of liquid crystal film 56 in turn causes a variation in the focal length of lens elements 40 and 46 to thereby vary the focusing power of multifocal ophthalmic lens 10. The variable voltage is controlled by tracking system 26 which detects the convergent position of the eyes of the user to vary the focusing power of multifocal ophthalmic lens 10 depending upon whether the user is viewing distant or near objects. Unlike bifocal lenses or trifocal lenses, the multifocal ophthalmic lens 10 of the present invention therefore provides a continuous range of varying focal lengths unlike the discrete focal lengths of bifocal and trifocal lenses. Multifocal ophthalmic lens 10 therefore compensates for the decrease in the accommodation power of the eyes of the user over a broad range of viewing distances. For example, through proper choices of the index of refraction of lens elements 40 and 46 and the selective actuation of liquid crystal film 56, multifocal ophthalmic lens 10 can provide corrected vision for ranges from 33 centimeters to nine feet of from 33 centimeters to infinite distance of other selected distances.

In the preferred embodiment, liquid crystal film 56 presents a 0.25 change in the index of refraction of multifocal ophthalmic lens 10. This change in the index of refraction results in approximately a 3 diopter change in the power of multifocal ophthalmic lens 10.

Referring to FIG. 2, in order to decrease the amount of ambient light reaching the eye of the user of multifocal ophthalmic lens 10 and to eliminate either the O-ray or E-ray depending upon the refractive index desired and presented by lens 10, polarizers 64 and 66 are provided. Polarizer 64 is mounted to inner concave surface of lens element 40, and polarizer 66 is mounted to outer convex surface 50 of lens element 46. Although FIG. 2 illustrates the use of both polarizers 64 and 66, in the alternative, either polarizer 64 or 66 may be utilized in connection with multifocal ophthalmic lens 10. Alternatively, one or more analyzers may be used in combination with polarizers 64 and 66. Polarizers 64 and 66 are lightly tinted so as to not decrease the transparency of multifocal ophthalmic lens 10 and may comprise for example, polarizers manufactured by Polaroid Corporation.

Figure 3:
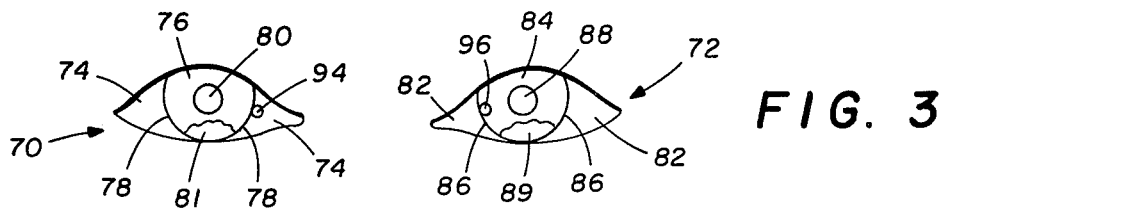
FIG. 3 is a diagrammatic illustration of the tracking system of the present invention for distant vision.

Referring simultaneously to FIGS. 3–7, wherein like numerals are utilized for like and corresponding portions of a human eye, the operation of tracking system 26 of the multifocal ophthalmic lens 10 of the present invention will now be described. Referring initially to FIG. 3, eyes 70 and 72 are diagrammatically illustrated. Eye 70 includes sclera 74, cornea 76 and limbus 78 which is the marginal region of the cornea of the eye by which it is continuous with the sclera. Eye 70 also includes pupil 80 which is the aperture in the center of iris 81 through which light is admitted into the eyeball. Similarly, eye 72 includes sclera 82, cornea 84, limbus 86, pupil 88 and iris 89.

Light sources 28 (FIG. 1) each cause a beam of light to be directed to impinge upon eyes 70 and 72. The intensity of the reflected beam from eyes 70 and 72 is detected by light detectors 30 (FIG. 1) associated with eyes 70 and 72 to control the amount of voltage applied to liquid crystal film 56 to thereby control the focusing power of multifocal ophthalmic lens 10. Light sources 28 project a beam of light that is fixed in relationship to the eyes of the user. FIG. 3 illustrates the positioning of the beams of light indicated by numerals 94 and 96 generated by light sources 28 when the user of multifocal ophthalmic lens 10 is looking at objects at a distance and straight ahead. Light beam 94 is positioned to impinge upon sclera 74 to the right of limbus 78 of eye 70. Light beam 96 is positioned to impinge upon cornea 84 to the right of limbus 86 of eye 72. Light beams 94 and 96 are fixed in position and are initially adjusted for each individual user to impinge upon the locations illustrated in FIG. 3 for distant viewing.

Since light beam 94 impinges upon sclera 74 which is the white portion of the eyeball, light detector 30 associated with eye 70 will detect a greater amount of reflected light from sclera 74 than will light sensor 30 associated with eye 72 for detecting reflected light from beam 96 which impinges upon the cornea 84. Since cornea 84 covers iris 89 which is the colored portion of the eye, more of light beam 96 will be absorbed by eye 72 than by eye 70. The variation in the amount of light detected by light detectors 30 is utilized to control the voltage applied to liquid crystal film 56 to vary the focusing power of multifocal ophthalmic lens 10.

Figure 4:
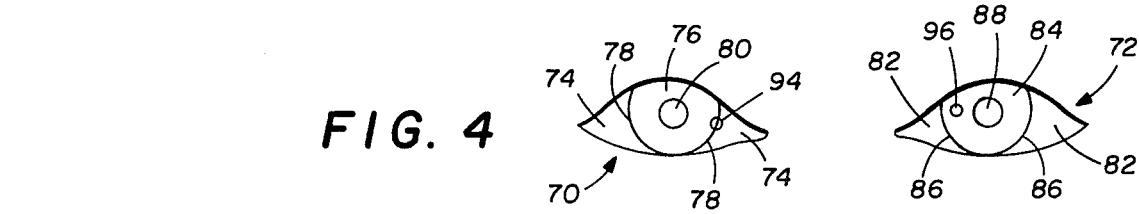
FIG. 4 is a diagrammatic illustration of the tracking system of the present invention for intermediate distant vision.

FIG. 4 illustrates the position of eyes 70 and 72 when an object at a closer proximity than the object being viewed in FIG. 3 is viewed. It can be seen that eyes 70 and 72 have moved closer together or converged to focus upon an object closer to the eyes. As a result, cornea 76 has moved toward the right such that light beam 94 now impinges upon limbus 78 to decrease the amount of light detected by light detector 30 associated with eye 70. Similarly, cornea 84 of eye 72 has converged toward the left such that light beam 96 impinges cornea 84 closer to pupil 88. Therefore, the total amount of light reflected and detected by light detectors 30 is less than the amount of light detected from the eyes 70 and 72 when in the position illustrated in FIG. 3.

Figure 5:
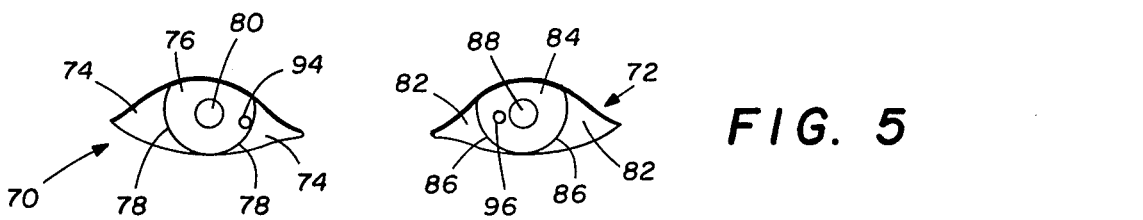
FIG. 5 is a diagrammatic illustration of the tracking system of the present invention for near vision.

FIG. 5 illustrates the position of eyes 70 and 72 when the user of multifocal ophthalmic lens 10 views an object in close proximity to eyes 70 and 72 such as for reading. Cornea 76 of eye 70 has converged further to the right. Light beam 94 now totally impinges upon cornea 76, such that no light is reflected from sclera 74 to light detector 30 associated with eye 70. Similarly, cornea 84 of eye 72 has converged toward the left closer to eye 70, such that light beam 96 now impinges cornea 84 closer to pupil 88 with respect to the position as illustrated in FIG. 4. FIG. 5 therefore illustrates the position of eyes 70 and 72 which presents the least amount of reflected light to light detectors 30. This reduced amount of reflection from corneas 76 and 84 results in a voltage change applied to liquid crystal film 56 to increase the focusing power of multifocal ophthalmic lens 10.

Figure 6:
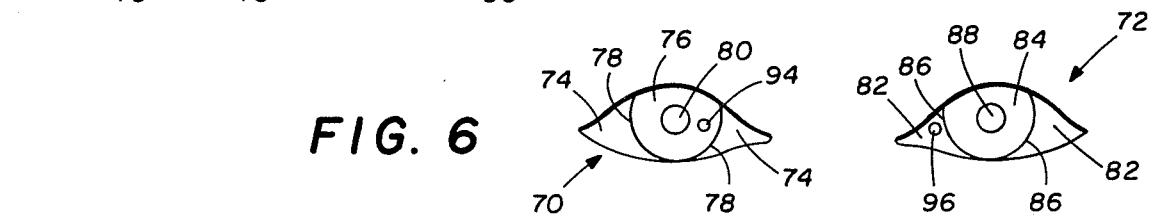
FIG. 6 is a diagrammatic illustration of the tracking system of the present invention for an abrupt left gaze.

FIG. 6 illustrates the position of eyes 70 and 72 with respect to light beams 94 and 96 when eyes 70 and 72 move to focus on an object to the left of eye 72. Cornea 84 has moved from the position illustrated in FIG. 3 to a position illustrated in FIG. 6 such that light beam 96 now impinges upon sclera 82 of eye 72. Similarly, cornea 76 of eye 70 has moved from the position shown in FIG. 3 to the position shown in FIG. 6 such that light beam 94 now impinges on cornea 76. Light detector 30 associated with eye 72 now receives a bright reflection from light beam 96 reflected from sclera 82. This increased reflection indicates to the tracking circuitry (FIG. 8) that an object is being viewed to the left of eyes 70 and 72. No voltage is then applied to liquid crystal film 56, such that multifocal ophthalmic lens 10 does not provide any increased focusing power to the user to this rapid eye movement.

Figure 7:
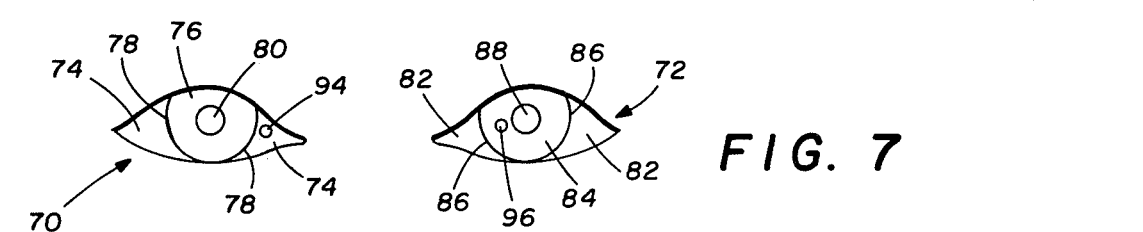
FIG. 7 is a diagrammatic illustration of the tracking system of the present invention for an abrupt right gaze.

FIG. 7 illustrates the position of eyes 70 and 72 when an object to the right of eyes 70 and 72 is viewed by the user of multifocal ophthalmic lens 10. In comparing the position of eyes 70 and 72 shown in FIG. 7 with the position illustrated in FIG. 3, it can be seen that light beam 94 now impinges upon sclera 74 of eye 70 and light beam 96 impinges upon cornea 84 of eye 72 closer to pupil 88 than positioned in FIG. 3. As in the case of a rapid left gaze, (FIG. 6), since light beam 94 now results in a maximum reflection to light detector 30 associated with eye 70, no voltage is applied to liquid crystal film 56 such that no increase in focusing power results when the user rapidly gazes to the right.

While the positioning of light beams 94 and 96 has been discussed in connection with FIGS. 3–7, it will be understood that alternate placements of beams 94 and 96 can be utilized to detect convergence of the cornea of one eye with respect to the cornea of the other eye. For example, light beams 94 and 96 may be both positioned on the corneas 76 and 84 of eyes 70 and 72 to determine the inward movement of eyes 70 and 72. Alternatively, light beams 94 and 96 may be focused to impinge upon the opposite edge of limbus 78 and 86 as illustrated in FIGS. 3–7.

Figure 8:
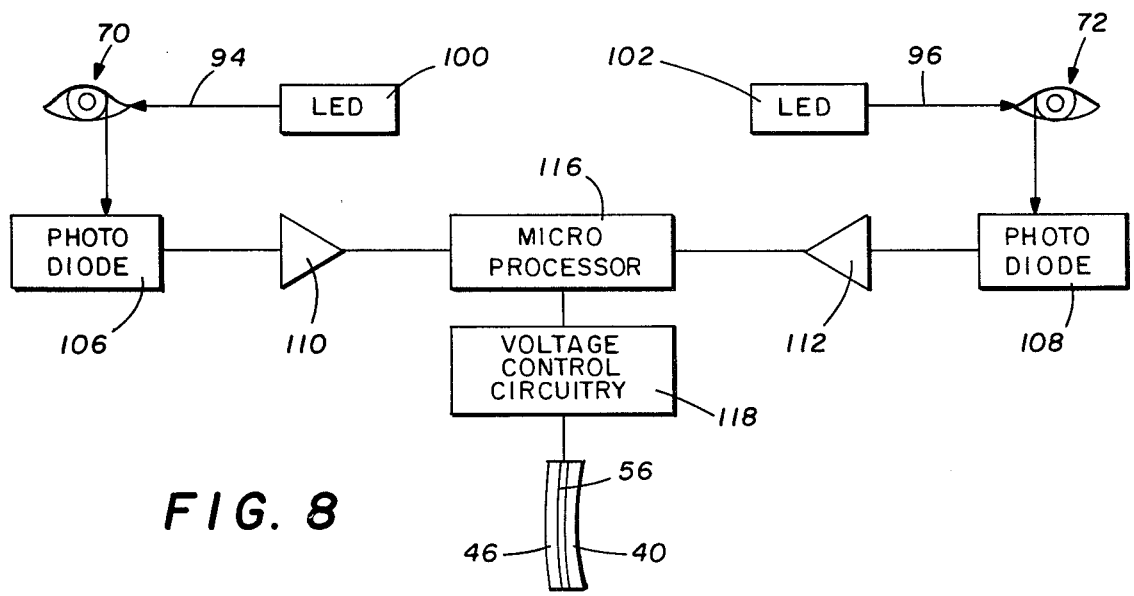
FIG. 8 is a block diagram of the circuitry utilized in the present tracking system.

FIG. 8 illustrates the circuitry of tracking system 26 of multifocal ophthalmic lens 10. Light sources 28 associated with lenses 10 may comprise for example, light emitting diodes 100 and 102 which may comprise visible red light emitting diodes or infrared light emitting diodes such as Model MD 50 manufactured and sold by Monsanto Corporation and Model MLED 930 manufactured and sold by Motorola Semiconductor Products, Inc. The output of light emitting diode 100 is light beam 94 which is reflected by eye 70 to be detected by light detector 30 associated with eye 70 which may comprise a photodiode 106. The output of light emitting diode 102 is light beam 96 which is reflected by eye 72 to impinge and be detected by light detector 30 associated with eye 72 which may comprise a photodiode 108. The output of photodiodes 106 and 108 are applied to linear voltage amplifiers 110 and 112 which may comprise, for example, Model LH101 manufactured and sold by National Semiconductor Corporation. Linear amplifiers 110 and 112 serve to amplify the output of photodiodes 106 and 108 depending upon the ambient light condition presented to multifocal ophthalmic lenses 10. The gain of the tracking system circuitry can be controlled by varying a biasing resistor associated with linear amplifiers 110 and 112 to increase the gain of the system in a dark ambient environment or decrease the gain of the system in a light ambient environment. Such a control can be conveniently placed on eyeglass frame 12 (FIG. 1) for adjustment by the user. The initial gain of the system can be set by directing light beams 94 and 96 onto the corneas 76 and 84 of eyes 70 and 72 to establish a null reference point for the system.

The outputs of amplifiers 110 and 112 are applied to a microprocessor 116. Microprocessor 116 may comprise for example, Model 8080 manufactured and sold by Intel Corporation. Microprocessor 116 is programmable in a manner well known to those skilled in the art to provide a corresponding output depending upon the relative intensity sensed by photodiodes 106 and 108 amplified by amplifiers 110 and 112 which reflect the convergent position of eyes 70 and 72.

The output of microprocessor 116 is applied to voltage control circuitry 118 which includes voltage supply source 32 for applying a variable voltage to liquid crystal film 56. The output of voltage control circuitry 118 applies a variable voltage to liquid crystal film 56 to thereby vary the index of refraction presented by liquid crystal film 56. Variation in the index of refraction presented by liquid crystal film 56 in turn causes the index of refraction of lens elements 40 and 46 to vary to thereby vary the focusing power of multifocal ophthalmic lens 10.

Although multifocal ophthalmic lens 10 has been described as being mounted into an eyeglass frame, alternatively, the lens of the present invention can be structured to "clip-on" to an existing eyeglass frame to reduce the cost in the manufacture of multifocal ophthalmic lenses of the present invention. In addition, lenses having various initial focal lengths can be utilized in the present multifocal ophthalmic lens to provide selected ranges of focusing powers.

Whereas the present invention has been described with respect to specific embodiments thereof, it will be understood that various changes and modifications will be suggested to one skilled in the art, and it is intended to encompass such changes and modifications as fall within the scope of the appended claims.

What is claimed is:

1. A pair of multifocal eyeglasses which utilizes varying focal lengths to provide accommodation for both near and far distances while allowing the user to view both near and far distances through the center of the lens or any part of the lens comprising:

a pair of first and second lens elements, said lens elements including a first liquid crystal layer disposed adjacent said first lens, a second liquid crystal layer disposed adjacent said second lens and first and second electrodes connected to each of said first and second liquid crystal layers, said first and second lenses being substantially coextensive with said first and second liquid crystal layers, respectively, said liquid crystal layers capable of changing in orientation to present a variable index of refraction under the action of an applied electric field;

a voltage supply source for applying a voltage to said electrodes to vary the index of refraction presented by said first and second liquid crystal layers, such that in response to application of said variable voltage to said electrodes, the focal length of said first and second lenses changes;

means for varying said voltage applied to said electrodes to determine the focal length of the lens elements including means for tracking the movement of the eyes of the user, such that a convergent movement of the eyes for near and distant vision and parallel lateral movement of both eyes is detected, said means for tracking the movement of the eyes including a first light source mounted adjacent said first lens element for generating a beam of light to impinge upon the sclera of the user's eye adjacent and to the side of the limbus of that eye when the user is looking straight ahead at distant objects, a second light source mounted adjacent said second lens element for generating a beam of light directed to impinge upon the cornea of the other eye of the user, adjacent and to the side of the limbus of that eye when the user is looking straight ahead at distant objects, and at least one photodiode light detector mounted adjacent each said lens element for detecting light from said first and second light sources that is reflected from each eye and for producing output signals; and means responsive to said tracking means for generating a control signal for application to said voltage supply source including amplifier means for amplifying the signals from said photodiodes and processing means for providing the control signal based upon the relative intensity of light sensed by said photodiodes, said processing means being programmed such that no change in the control signal occurs when parallel lateral movement of both eyes is detected to prevent unwanted change of the focal length of said lens.

2. The pair of multifocal opthalmic eyeglasses recited in claim 1 wherein the means responsive to said tracking means includes means for adjusting the gain of the system to compensate for dark and light ambient environments.

3. The pair of multifocal opthalmic eyeglasses as recited in claim 2 wherein said means for adjusting the gain of the system includes a biasing resistor associated with said amplifier means.

* * * * *